United States Patent [19]

Ritter et al.

[11] Patent Number: 5,522,971
[45] Date of Patent: Jun. 4, 1996

[54] DRY NEUTRALIZATION OF OLEFINICALLY REACTIVE ORGANIC LIQUID PHASES

[75] Inventors: Wolfgang Ritter, Haan; Stefanie Ortanderl, Juechen, both of Germany

[73] Assignee: Henkel Kommanditgesellschaft auf Aktien, Duesseldorf, Germany

[21] Appl. No.: 244,680

[22] PCT Filed: Dec. 2, 1992

[86] PCT No.: PCT/EP92/02785

§ 371 Date: Jun. 7, 1994

§ 102(e) Date: Jun. 7, 1994

[87] PCT Pub. No.: WO93/12066

PCT Pub. Date: Jun. 24, 1993

[30] Foreign Application Priority Data

Dec. 7, 1991 [DE] Germany ............... 41 40 373.8

[51] Int. Cl.$^6$ .............. B01D 3/34; B01D 3/38; C07C 67/48
[52] U.S. Cl. .............. 203/14; 203/33; 203/36; 203/37; 203/38; 203/92; 203/95; 560/218
[58] Field of Search ............ 203/33, 34, 36, 203/37, 38, 95, 92, DIG. 16, DIG. 21, 14; 560/224, 218; 210/767, 774

[56] References Cited

U.S. PATENT DOCUMENTS

| | | | |
|---|---|---|---|
| 5,159,106 | 10/1992 | Ritter et al. | 560/224 |
| 5,198,574 | 3/1993 | Ritter et al. | 560/224 |
| 5,207,874 | 5/1993 | Hess et al. | 203/DIG. 21 |
| 5,210,281 | 5/1993 | Ritter et al. | 560/218 |
| 5,225,049 | 7/1993 | Barmentlo et al. | 203/DIG. 21 |

FOREIGN PATENT DOCUMENTS

| | | |
|---|---|---|
| 2330435 | 1/1975 | Germany. |
| 3843854 | 6/1990 | Germany. |
| 3843930 | 6/1990 | Germany. |
| 3843938 | 6/1990 | Germany. |
| 3843843 | 7/1990 | Germany. |
| 3939163 | 5/1991 | Germany. |
| 3939162 | 5/1991 | Germany. |
| 3939161 | 5/1991 | Germany. |
| 9007484 | 7/1990 | WIPO. |

*Primary Examiner*—Virginia Manoharan
*Attorney, Agent, or Firm*—Ernest G. Szoke; Wayne C. Jaeschke; Real J. Grandmaison

[57] ABSTRACT

Pure, substantially neutral, low-volatile organic compounds including reactive double bonds are advantageously isolated from a liquid feedstock which contains said compounds in combination with acidic reaction components or auxiliary materials by (i) adding to the feedstock, as neutralizing agents, finely powdered oxides, carbonates and/or hydroxides of the alkali metals and/or alkaline earth metals; (ii) adding, at the same time as the addition of the neutralizing agents or thereafter, a limited amount of water to the mixture of feedstock and neutralizing agents; (iii) mechanically mixing the liquid and solid mixture thus formed for at least a few minutes; (iv) distilling off water from the hot reaction mixture under reduced pressure; and (v) removal from the liquid product of the solid phase now present. Pure products which even without distillation exhibit low residual acid values in combination with low color values result. In a particular embodiment, a process according to the invention is used for an exchange of inhibitors in a mixture reactive when initiated by free radicals; in this exchange, a preparation inhibitor capable of undergoing a salt formation with bases is exchanged for an application inhibitor that may be freely selected with respect to kind and amounts thereof.

17 Claims, No Drawings

DRY NEUTRALIZATION OF OLEFINICALLY REACTIVE ORGANIC LIQUID PHASES

FIELD OF THE INVENTION

This invention relates to an improvement in the recovery, in the pure state, of substantially neutral low-volatile organic components prone to undergo polymerization and/or gelling, which components comprise reactive olefinic double bonds. More particularly, the invention is intended to provide the isolation in the pure state of those components, the purification of which is not possible or not readily possible by means of a distillation. The problems to be solved by the invention are described hereinbelow by way of example for the substance class of polyolacrylic acid esters. However, it will be readily intelligible to one skilled in the art that the area of application of the invention is not restricted to this particular class of substances. The corresponding esters of crotonic acid are another example.

STATEMENT OF RELATED ART

For producing polyol(meth)acrylic acid esters, polyfunctional alcohols are esterified with acrylic acid and/or methacrylic acid—hereinbelow designated as (meth)acrylic acid—in the presence of suitable catalysts and inhibitors and in the presence of an entraining agent, for example toluene and/or xylene. Inherent disadvantages are the concomitant use of solvents and/or entraining agents and the need of removing excessive (meth)acrylic acid and the acidic catalyst—conventionally p-toluenesulfonic acid—from the crude product by washing with an alkaline medium.

The publications DE-A1-38 43 854, DE-A1-38 43 938, DE-A1-38 43 930 and DE-A 1-38 43 843 describe possible improvements in the preparation of such polyfunctional (meth)acrylic acid esters without using any solvents. In addition to this option of absolutely avoiding the use of solvents, there is another process advantage in that acidic substances present in the crude reaction mixture—for example residual amounts of the (meth)acrylic acid, acidic catalysts and/or inhibitors exhibiting an acidic reaction—can be removed without a step of washing, by a so-called dry neutralization. Details of this process modification are described in DE-A1-39 39 162 and DE-A1-39 39 163.

In the process described, for example, in the first mentioned printed publication, under optimized conditions, the crude reaction product having an acid value of about 40—caused by an excess of acrylic acid, p-toluenesulfonic acid and phenolic production inhibitors, especially di-tert-butylhydroquinone—is admixed with a twofold molar excess, relative to the acid value, of (anhydrous) calcium hydroxide at 80° C. The resulting mixture is allowed to react for about 1 hour, and then the water of neutralization is stripped off, and calcium salts of said acidic components are removed frown the reaction mixture by filtration. This process has the advantages of that the acidic components are almost completely removed, the product after filtration has a good color, and all of the by-products are concentrated in the filter cake.

The disadvantages of this embodiment of the dry neutralization reside in the relatively long duration of the filtration and in a comparably high loss of valuable product in the filter cake. Thus, the process described in DE-A1-39 39 162 may require filtration periods of several hours in a 1 kg laboratory test (usually from 2 to 4 hours), and the product losses may amount to between 10 and 15% by weight.

DESCRIPTION OF THE INVENTION

Object of the Invention

It is the object of the present invention to substantially reduce the deficiencies shown here of the dry neutralization, without basically having to compromise the advantages of the described type of process. More specifically, the teaching of the invention is to optimize the process for preparing the reaction products of the type described as undistillable and prone to gelling, so that with short filtration times and low expenditure on filters lower amounts of filter cakes are obtained and, consequently, low losses of valuable materials occur.

SUMMARY OF THE INVENTION

The teaching according to the invention is based on the finding that the neutralizing step and the subsequent removal of the filter cake as described can be considerably facilitated, if low amounts of water are introduced into this neutralization step and if a definite sequence of process steps as described in detail hereinbelow is maintained. As a result, the invention specifically achieves two significant improvements: The duration of the neutralization can be substantially abridged, while successfully at the same time the amount of solids to be removed and, thus, of the produced filter cake are substantially reduced. Simultaneously, the inevitable product loss is decreased accordingly, without having to resort to undesirable auxiliary means or working aids such as solvents, washing operations and the like.

Thus, the present invention relates to a process for the isolation of pure, substantially neutral, low-volatile organic compounds comprising reactive olefinic double bonds from a feedstock which contains said compounds in combination with minor amounts of acidic reaction components and/or corresponding auxiliary materials in a liquid phase, said process comprising the steps of neutralization, removal of the resulting salts and recovery of pure products which, even without distillation, exhibit low residual acid values in combination with low color values, by using finely powdered oxides, carbonates and/or hydroxides of the alkali metals and/or alkaline earth metals—hereinbelow designated as "neutralizing agents"—and the subsequent separation of the organic liquid phase from the resulting solid phase.

The process according to the invention is characterized in that the step of neutralization is effected as follows:

Addition of the solid neutralizing agent to the hot feedstock, with the neutralizing agent being used in an at least stoichiometric amount, relative to the acid value of the feedstock;

addition, at the same time or thereafter, of a limited amount of water to the reaction mixture;

conducting and at least largely completing the neutralization by mixing the material mixture for a period of at least some minutes;

distilling off an at least substantial proportion of the water from the hot reaction mixture under reduced pressure, and finally removal of the solid phase now present in the reaction mixture in an optional manner, appropriately by means of filtration.

DESCRIPTION OF PREFERRED EMBODIMENTS

In one embodiment, the invention relates to the application of this process to the production of commercial products which may be of practical importance as, for example, UV-curable varnish systems. In another important embodiment the invention, more specifically, is intended to enable a partial or preferably full exchange of free radical inhibitors—so-called preparation inhibitors—from mixtures thereof with compounds reactive upon free radical initiation, especially polymerizable and/or cross-linkable, olefinically mono- and/or polyunsaturated compounds, for other inhibitors or inhibitor systems to free radicals—hereinbelow also called application inhibitors—which are subject to free choice with respect to kind and amounts thereof. This application of the process according to the invention is important with respect to an exchange of preparation inhibitors having a limited physiological compatibility for application inhibitors that are physiologically more tolerable. This aspect of the invention may be of particular importance in connection with curable and/or cured systems or molded parts such as adhesives or solid surgical auxiliary materials intended to be used in direct contact with the human and/or animal living body.

One essential element of the process according to the invention is the controlled addition of low amounts of water to the reaction mixture to facilitate the neutralization reaction and the subsequent filtration. However, in order to obtain an optimum result, the sequence of adding the solid neutralizing agent and the low amount of water in accordance with the invention is important. Here, the invention teaches first to admix the solid neutralizing agent at least in the amount stoichiometrically required to the crude reaction material to be neutralized, and only then to add the water as a reaction aid. Comparative tests showed that reversing this sequence increases the danger of gelling, depending on the amount of water, and/or water cannot develop its property as a reaction aid, whereas adding both water and neutralizing agent at the same time to the feedstock often results in a prolongation of the periods required for the filtration in the subsequent separating step. Nevertheless, the invention also contemplates such an addition at the same time of neutralizing agent and water; even then it may be preferred beforehand to add at least part of the solid neutralizing agent.

The operational steps of the process according to the invention themselves may be carried out in a relatively wide range of working temperatures. All temperatures of from about room temperature to about 140° C. are taken into consideration. The selection of a respective optimum temperature will depend, inter alia, on the viscosity of the liquid phase to be treated. Thus, it may be preferable to maintain the feedstock at elevated temperatures during said operational steps, especially at temperatures of at least 50° C. On the other hand, it should be avoided that the working temperatures would become too high, with about 100° C. to 120° C. to be especially mentioned as an upper limit. For operation in practice, temperatures within a range of about from 70° C. to 90° C. and especially within a range of around 80° C. have proven to be especially appropriate. The proper selection of the temperature may affect the period of reaction and the duration of the filtration step, on the one hand; however, on the other hand, attention should also be given to the color of the reaction product as ultimately desired. In a number of fields of use—for example when varnishes are produced—it is important that the reaction product obtained for final use be of bright color. This parameter can be especially influenced by controlling the temperature of the process according to the invention.

A further preferred measure according to the invention may become particularly important if reaction products highly prone to gelling, which products have been inhibited with aerobically active inhibitors—for example those of the phenol type—that are active only in the presence of oxygen, are intended to be subjected to the treatment. In this case the invention teaches that air is to be bubbled through the feedstock at least during the addition of neutralizing agent and water and the subsequent neutralization. Thus, it may be expedient to heat the crude product in the reactor to about 80° C. and simultaneously to introduce air. The following reaction steps are also carried out with continuous introduction of air. Thereby the danger of an undesirable gelling even of highly reactive crude reaction products can be efficiently eliminated. If anaerobically active inhibitors such as, for example, phenothiazine are employed, air must not be introduced.

The amount of the solid neutralizing agent added in the first process step is preferably limited so that not more than about 1.5 times the amount stoichiometrically required is added. The lowest amount of the neutralizing agent to be added conforms to the stoichiometric amount, if the complete neutralization of the acidic components capable of undergoing salt formation is required. In an especially important embodiment of the teaching according to the invention, the amount of the solid neutralizing agent is determined so that about 1.1 to 1.3 times the required stoichiometric amount is used. Thereby, the amount of the resulting filter cake is limited to the extent necessary, while at the same time—upon the concomitant action of the amount of water employed according to the invention—it is ensured that a complete neutralization is effected.

At the same time as, or preferably after, the addition of the at least largely dry neutralizing agent, the water is added to the hot reaction batch in an amount of about from 0.5 to 15% by weight, and preferably in an amount of about frown 2 to 10% by weight, with the figures in % by weight being based on the amount of feedstock. The addition of about from 3 to 7% by weight of water to the feedstock may be particularly suitable. In practical operation, about 5% of water will be often employed. Larger amounts of water would increase the period of time required for the subsequent removal by distillation of the water. Losses of product may be associated therewith. Lower amounts of water, more specifically, may adversely affect the filtration time.

The period of time required for the neutralization reaction to be completed under the operation conditions according to the invention usually is not more than 30 minutes at most and in general is within the range of from about 10 to 20 minutes. Care is to be taken that the polyphasic reaction mixture is sufficiently mixed during this reaction step. In consideration of all of these variables, the modification according to the invention of the neutralization step is described as follows:

The crude reaction product is heated in the reactor at about 80° C., while air is introduced. To the crude product there is added about 1.2 times the amount (relative to the initial acid value) of a hydroxide in the solid state of alkali metals or alkaline earth metals. immediately thereafter, about 5% by weight of water is added to the mixture. Then the resulting mixture is stirred at 80° C. for a period of about 15 minutes to effect neutralization. After the completion of this neutralization step, water—i.e., both the water formed in the neutralization reaction and, at least in pan, the water intentionally added according to the invention—is distilled off at 80° C. in the course of about 15 to 30 minutes.

The resulting product is a slurry of a solid salt in the neutralized liquid reaction stock. This mixture of substances is subjected to a phase separation, wherein the solids portion is appropriately removed through a filter. Especially suitable to serve this purpose are pressurized filters operated, for example, at a superatmospheric pressure of several bars.

In comparison to the dry neutralization procedures which are reported in the literature initially described, the neutralization process according to the invention allows for substantial improvements with respect to the time required for the filtration as well as with respect to the product losses. Thus, for example, in comparative runs the duration of the filtration may be reduced from about 1 hour to a period of 2 minutes. The product loss due to the removed filter cake is distinctly below 10 to 15% by weight, for example within a range around 3% by weight, each relative to the crude reaction product.

Particular importance is attached to the use of finely divided, and especially finely powdered, oxides and/or hydroxides of calcium and/or magnesium in the operation of the process according to the invention. Among the compounds of these two alkaline earth metals, the respective calcium compounds are of more particular importance. In a preferred embodiment of the invention, finely divided solids are introduced into the neutralization step, which at least in part contain calcium compounds of the type mentioned. In an especially important embodiment, calcium hydroxide ($Ca(OH)_2$) and/or burnt lime (CaO) is used. It is especially a finely divided calcium hydroxide that frequently provides an optimum balance among the process parameters, which in fact are mutually conflicting, that relate to residual acid value, color value, thermal stressability, duration of the process, amount of the dry neutralizing agent to be employed, and the like.

Distillation for removing the water after the neutralization reaction is conveniently carried out at sufficiently reduced pressures in the specified temperature range above 50° C. A suitable pressure range is from about 1 to about 150 mbar, while the operation within a range of about from 20 to 150 mbar and especially within a range of about from 20 to 100 mbar may be particularly preferred. Thereby it is possible successfully to reduce the residual water content in the final product to below about 0.1% by weight.

As has already been set forth, the modification, according to the invention, of the neutralization step is important not only for the large scale production of commercial products as described, for example, in DE-A1-39 39 163. The modification according to the invention also may be of particular importance for the inhibitor exchange within the scope of the teaching of DE-A1-39 39 162. This is always possible, if the so-called preparation inhibitors employed are compounds which are capable of forming salts under the conditions of the neutralization reaction and, hence, are capable of being bound into the filter cake to be removed. As to details, reference may be made to said printed publications. Here, it may be repeated as only an abstract: In the embodiment concerned here, the neutralization treatment and the possibility created thereby of a simple phase separation succeeds in the depletion or even complete removal from the feedstock mixture of the preparation inhibitor. This enables the application inhibitor to be freely selected with respect to kind and/or amount thereof.

Phenol compounds comprising free hydroxyl groups capable of undergoing salt formation are one class, known in polymerization technology, of compounds having a pronounced aerobic inhibitor activity against initiation of reactions via free radicals in olefinically unsaturated systems. Particularly active representatives are found in the class of the hydroquinone compounds, especially the ring-substituted hydroquinone compounds. Alpha-substituted hydroquinones, and among these dialkyl-substituted compounds of this kind, are especially reactive and, for this reason, are especially suitable for a use as preparation inhibitor. This inhibitor class is distinguished by a high inhibitive action against an undesirable free radical-initiated polymerization. A representative compound exhibiting a particularly high inhibitor action, for example, is 2,5-di-tert-butylhydroquinone, which may be added for stabilization in the stage of the preparation of the reactive systems in amounts that are subject to a virtually free selection. As a consequence of the subsequent separation, within the scope of the invention, of such salt-forming inhibitors by at least partial attachment to a solid precipitant followed by phase separation, it becomes possible to exchange the preparation inhibitor for application inhibitors that are subject to free choice with respect to kind and amounts thereof.

Such an exchange may become especially meaningful, if for some application the physiological acceptability of reactive systems needs to be checked, as is the case, for example, in the technology of adhesives for use in the living organism. Here, adhesives or adhesive systems are required which contain physiologically highly acceptable application inhibitors. One particularly suitable inhibitor is vitamin E, the use of which, for purposes here referred to, is described in detail in DE-A1-39 39 161.

EXAMPLES

Example 1

A crude reaction product (1,000 g), prepared by solvent-free esterification of trimethylolpropane +3 EO according to the teaching of DE-A1-38 43 854 with an excess of 20% by moles of acrylic acid, with the use of 3.5% by weight of p-toluenesulfonic acid as a catalyst and of 2,000 ppm of 2,5-di-tert-butylhydroquinone as an inhibitor, and having an acid value of 30, is heated to 80° C. 1.5 times the stoichiometric amount of solid powdery calcium hydroxide is added at once. Then, 10% by weight of water, relative to the total amount, is added. The resulting mixture is stirred for 30 minutes. Then the water is removed at 50 mbar within 30 minutes, during which period the mixture is stirred (propeller agitator, 400 rpm), while 40 l/hour of air are bubbled through the product. The resulting solid phase is removed via a 2 l-pressurized filter (filter area of 0.01 m$^2$) under 3 bar. The resulting product has the following characteristics: Acid value 0.05; color value (Gardner) <1; water content 0.4% by weight. The filtration time is about 20 minutes, while the product loss amounts to about 6% by weight.

Example 2

One thousand grams of a crude reaction product, having an acid value of 30, prepared in accordance with the description of Example 1, except with the use of polyethyleneglycol as the polyfunctional alcohol, is heated to 80° C. 1.3 times the stoichiometric amount of solid powdery calcium hydroxide and 0.5 times the stoichiometric amount of solid powdery magnesium hydroxide are added at once. Then, 3% by weight of water, relative to the total amount, is added. The resulting mixture is stirred for 30 minutes. Then the water is removed at 50 mbar within 30 minutes, during which period the mixture is stirred (propeller agitator, 400 rpm), while 40 l/hour of air are bubbled through the product. The resulting solid phase is removed via a 2 l-pressurized filter (filter area of 0.01 m$^2$) under 3 bar. The resulting product has the following characteristics: Acid value 0.2; color value (Gardner) <1; water content 0.15% by weight. The filtration time is about 2 minutes, while the product loss amounts to about 3% by weight.

Example 3

The crude reaction product of Example 1, having an acid value of 30, is now employed in an amount of 100 kg and is heated to 80° C. Then, 1.2 times the stoichiometric amount of solid powdery calcium hydroxide is added all at once. Then, 5% by weight of water, relative to the total amount, is added. The resulting mixture is stirred for 30 minutes. Then the water is removed at 50 mbar within 30 minutes, during which period the mixture is stirred (4 stage MIG stirrer), while 400 l/hour of air are bubbled through the liquid product phase. The resulting solid phase is removed via a 160 l pressurized filter (filter area of 0.5 m$^2$) under 2 bar. The resulting product has the following characteristics: Acid value 0.1; color value (Gardner) <1; water content 0.3% by weight. The filtration time is about 11 minutes, while the product loss amounts to about 3.5% by weight.

Example 4

One thousand grains of a crude reaction product having an acid value of 30, prepared in accordance with the description of Example 1, except with the use of neopentylglycol +2 PO as the polyfunctional alcohol component, is heated to 80° C. Then, 0.9 times the stoichiometric amount of solid powdery calcium hydroxide and 0.5 times the stoichiometric amount of solid powdery magnesium hydroxide are added at once. Then, 3% by weight of water, relative to the total amount, is added. The resulting mixture is stirred for 30 minutes. Then the water is removed at 50 mbar within 30 minutes, during which period the mixture is stirred (propeller agitator, 400 rpm), while 40 l/hour of air are bubbled through the liquid product. The resulting solid phase is removed via a 2 l pressurized filter (filter area of 0.01 m$^2$) under 3 bar. The resulting product has the following parameters: Acid value 0.9; color value (Gardner) 1; water content 0.5% by weight. The filtration time is about 1 minute, while the product loss amounts to about 3% by weight.

Example 5

The crude reaction product of Example 1 in an amount of 1,000 g is heated to 90° C. Then, 1.2 times the stoichiometric amount of solid powdery calcium hydroxide is added in combination with 5% by weight of water, relative to the total amount, as a slurry all at once. The resulting mixture is stirred for 30 minutes. Then the water is removed at 50 mbar within 30 minutes, during which period the mixture is stirred (propeller agitator, 400 rpm), while 40 l/hour of air are bubbled through the product. The resulting solid phase is removed via a 2 l pressurized filter (filter area of 0.01 m$^2$) under 3 bar. The resulting product has the following characteristics: Acid value 0.3; color value (Gardner) <1; water content 0.5% by weight. The filtration time is about 2 minutes, while the product loss amounts to about 3% by weight.

Example 6

One thousand grams of a crude reaction product having an acid value of 25, prepared in accordance with the description of Example 1, except with the use of bisphenol-A as the polyfunctional alcohol, is heated to 80° C. 1.5 times the stoichiometric amount of solid powdery calcium hydroxide is added at once. Then, 2% by weight of water, relative to the total amount, is added. The resulting mixture is stirred for 30 minutes. Then the water is removed at 50 mbar within 30 minutes, during which period the mixture is stirred (propeller agitator, 400 rpm), while 40 l/hour of air are bubbled through the product. The resulting solid phase is removed via a 2 l pressurized filter (filter area of 0.01 m$^2$) under 3 bar. The resulting product has the following characteristics: Acid value 0.2; color value (Gardner) 3 to 4; water content 0.5% by weight. The filtration time is about 5 minutes, while the product loss amounts to about 4% by weight.

The invention claimed is:

1. A process for the purification of substantially neutral, low-volatile organic compounds comprising reactive double bonds from a feedstock which contains said compounds in combination with minor amounts of acidic components in a liquid phase having a known acid value, said process comprising steps of:

(A) adding to feedstock having a temperature between room temperature and 140° C. a finely powdered solid neutralizing agent selected from the group consisting of alkali metal oxides, alkali metal carbonates, alkali metal hydroxides, alkaline earth metal oxides, alkaline earth metal carbonates, and alkaline earth metal hydroxides in an at least stoichiometric amount, relative to the acid value of the feedstock, so as to form with the feedstock an undistillable reaction mixture;

(B) adding, at the same time as step (A) or thereafter from about 0.5 to 15% by weight, based on the amount of feedstock, of water to the reaction mixture so as to facilitate the neutralization in step (A) and subsequent separation of a solid phase;

(C) mixing the mixture from step (B) for a period of from 10 to 30 minutes;

(D) distilling off water from the mixture under reduced pressure, so as to form a product containing both liquid and end solid phases, and (E) separating the solid phase from the product.

2. A process according to claim 1 wherein the feedstock further contains aerobically active inhibitors, and the feedstock is purged with air at least during steps (A) through (C).

3. A process according to claim 1, wherein the amount of the neutralizing agent—relative to the acid value of the feedstock—is within the range of from about 1.1 to 1.3 times the amount of the neutralizing agent stoichiometrically required.

4. A process according to claim 3, wherein water is added in an amount of from about 2 to 10% by weight based on the amount of feedstock.

5. A process according to claim 4, wherein the solid phase is separated from the liquid phase by filtration under pressure and at temperatures within the temperature range of about from 70° C. to 90° C.

6. A process according to claim 1 wherein the alkali metal oxide is calcium oxide or magnesium oxide, and wherein the alkali metal hydroxide is calcium hydroxide or magnesium hydroxide.

7. A process according to claim 6, wherein water is distilled off from the mixture at final pressures within a range of from bout 1 to 150 mbar.

8. A process according to claim 1, wherein the organic compound comprises substantially anhydrous olefinically unsaturated compounds prone to polymerization or gelling and contains, as acidic components residual amounts of acid from condensation, acidic catalysts, or inhibitors showing acidic reactions.

9. A process according to claim 1, wherein the organic compound comprises low-volatile esters from polyfunctional alcohols and olefinically unsaturated carboxylic acids.

10. A process according to claim 1 wherein during said process steps (A) to (E) the temperature is maintained within a temperature range from 50° to 120° C.

11. A process according to claim 10, wherein during said process steps (A) to (E) the temperature is maintained within a temperature range from 70° to 90° C.

12. A process according to claim 1, wherein the solid phase is separated from the liquid phase by filtration under pressure and at temperatures in excess of 50° C.

13. A process according to claim 1, wherein water is distilled off from the mixture at final pressures within a range of from about 1 to 150 mbar.

14. A process for the purification of substantially neutral, low-volatile organic compounds comprising reactive double bonds from a feedstock which contains said compounds in combination with a free radical inhibitor capable of salt formation and minor amounts of acidic components in a liquid phase having a known acid value, said process comprising the steps of:

(A) adding a physiologically acceptable inhibitor to said feedstock;

(B) adding to said feedstock at a temperature of between room temperature and 140° C. a finely powdered solid neutralizing agent selected from the group consisting of alkali metal oxides, alkali metal carbonates, alkali metal hydroxides, alkaline earth metal oxides, alkaline earth metal carbonates, and alkaline earth metal hydroxides in an at least stoichiometric amount, relative to the acid value of the feedstock, so as to form with the feedstock an undistillable reaction mixture;

(C) adding at the same time as step (B) or thereafter, from about 0.5 to 15% by weight, based on the amount of feedstock, of water to the reaction mixture so as to facilitate the neutralization in step (B) and subsequent separation of a solid phase;

(D) mixing the mixture from step (C) for a period of up to 30 minutes;

(E) distilling off water from the mixture under reduced pressure so as to form a product containing both liquid and solid phases; and (F) separating the solid phase from the mixture.

15. The process as in claim 14 wherein said feedstock contains phenol or hydroquinone compounds as said free radical inhibitor.

16. The process as in claim 14 wherein said feedstock contains dialkyl-substituted hydroquinones as said free radical inhibitor.

17. The process as in claim 14 wherein said physiologically acceptable inhibitor is vitamin E.

* * * * *